United States Patent
McKee et al.

(10) Patent No.: US 8,318,112 B2
(45) Date of Patent: Nov. 27, 2012

(54) SYSTEM AND PROCESS OF LIGHT CHAIN HYDROCARBON SYNTHESIS

(75) Inventors: William C. McKee, Junction City, KS (US); Kenneth R. Boyd, Linn Valley, KS (US); Steven J. Berger, Manhattan, KS (US)

(73) Assignee: Hydrocarbons Unlimited, LLC, Junction City, KS (US)

( * ) Notice: Subject to any disclaimer, the term of this patent is extended or adjusted under 35 U.S.C. 154(b) by 395 days.

(21) Appl. No.: 12/439,659

(22) PCT Filed: Sep. 3, 2007

(86) PCT No.: PCT/US2007/077479
§ 371 (c)(1),
(2), (4) Date: Mar. 2, 2009

(87) PCT Pub. No.: WO2008/030784
PCT Pub. Date: Mar. 13, 2008

(65) Prior Publication Data
US 2010/0210885 A1  Aug. 19, 2010

(51) Int. Cl.
*B01J 8/04* (2006.01)
*C07C 1/02* (2006.01)

(52) U.S. Cl. ........ 422/608; 422/621; 422/630; 422/631; 518/702; 585/310

(58) Field of Classification Search .............. 422/630, 422/631, 608, 621; 585/310; 518/702
See application file for complete search history.

(56) References Cited

U.S. PATENT DOCUMENTS

| | | | | |
|---|---|---|---|---|
| 2,080,981 | A | * | 5/1937 | Haas ............................. 423/176 |
| 4,140,602 | A | * | 2/1979 | Lewis et al. .............. 204/157.47 |
| 4,776,171 | A | * | 10/1988 | Perry et al. ...................... 60/698 |
| 4,927,856 | A | * | 5/1990 | Elion ............................ 518/702 |
| 5,964,985 | A | | 10/1999 | Wooten |
| 6,013,158 | A | | 1/2000 | Wooten |
| 6,942,719 | B2 | | 9/2005 | Steward |
| 7,153,432 | B2 | | 12/2006 | Kohler |
| 2004/0202738 | A1 | | 10/2004 | Gow et al. |

FOREIGN PATENT DOCUMENTS

DE  19522083 A1 * 10/1996

* cited by examiner

*Primary Examiner* — Jennifer A Leung
(74) *Attorney, Agent, or Firm* — Intellectual Property Center, LLC; Arthur K. Shaffer (57) ABSTRACT

The invention relates to a system and process for producing liquid hydrocarbons from a calcium carbonate feed-stock involving (i) liberation of a carbon dioxide gas from the heated calcium carbonate feedstock; (ii) filtering impurities from the extracted carbon dioxide of step (i); (iii) reacting the extracted carbon dioxide obtained in step (i) with a dihydrogen gas to form a methanol feedstock; (iv) isolating the cooled methanol feedstock formed in step (iii); (v) catalytically converting at least part of the methanol feedstock obtained in step (iii) at elevated temperature and pressure into aliphatic and aromatic liquid hydrocarbons; and (vi) isolating the decompressed liquid hydrocarbon product obtained in step (v).

1 Claim, 7 Drawing Sheets

SYSTEM AND PROCESS OF LIGHT CHAIN HYDROCARBON SYNTHESIS

FIELD OF THE INVENTION

This invention is directed to an improved system and process for producing a light chain hydrocarbon and more specifically for producing methanol and light chain hydrocarbons by a catalytic reaction.

BACKGROUND OF THE INVENTION

Oil, natural gas and coal are a source of fossil fuels and major sources of energy in the United States. These materials are also used to create gasoline and diesel fuel which provide energy for most forms of transportation and for synthetic materials, plastics and pharmaceuticals. However, these natural sources are being depleted rapidly. The increasing populations and the increased standards of living and demands for energy in developing countries are putting increased pressure on our diminishing fossil fuel resources and making them even more costly. Whereas coal reserves may last for another two or three centuries, readily accessible oil and gas reserves may not last that long. It therefore would be beneficial to provide readily accessible alternative sources of fuel using a non-depleted source.

Using hydrogen as an alternative fuel source has been discussed, for example by generating hydrogen using electrolysis. By utilizing hydrogen gas to provide energy to fuel cells or in a combustion process, electricity may be generated. While hydrogen is a clean source of combustion fuel, hydrogen has certain undesired attributes due to its volatility and reactive characteristics. Storing, transporting and delivering energy in the form of hydrogen has serious limitations. The handling of the volatile and potentially explosive material requires special conditions such as high pressure, cryogenic tanks and special materials to minimize diffusion and leakage. In addition, hydrogen must be handled carefully to avoid injury and damage, increasing the overall cost of the material. In order to dispense and utilize gaseous hydrogen, additional infrastructure may also be needed to produce, transport, store and dispense the hydrogen gas. Therefore, it would be beneficial to provide an alternative liquid hydrocarbon fuel product which can use existing infrastructure for production, transportation, storage and dispensing and which is not as volatile as hydrogen.

Processes for the conversion of (gaseous) hydrocarboneceous feedstocks, especially methane from natural sources, e.g. natural gas and/or coalbed methane, into liquid products, especially methanol and liquid hydrocarbons, are generally known. At ambient temperature and pressure, these hydrocarbons may be gaseous, liquid or (often) solid. However, these processes typically require transportation of the gaseous feedstocks which presents its own safety concerns and is similar to those of hydrogen. Transportation of the gas, e.g. through a pipeline or in the form of a liquefied natural gas, requires an extremely high capital expenditure or may simply not be practical. This holds true for low volume gas producers and/or fields. In addition, the burning of some gases has become an undesired option in view of the depletion of hydrocarbon sources, global warming and air pollution.

Annually, more than 20 billion tons of $CO_2$ are released into the atmosphere as a result of human activity, including electrical generation, industrial processes, transportation, and heating and cooling. In addition, when hydrocarbons are burned they produce $CO_2$ and water, adding to the build-up of carbon dioxide and other greenhouse gases which may contribute to global warming. While photosynthesis from increased terrestrial biomass may help decrease the effects of these excess greenhouse gases, it is not expected to keep up with rates of $CO_2$ production. Therefore, it would be beneficial to provide a chemical synthesis reaction which reverses or stabilizes the build-up of $CO_2$ and produces efficient and economical hydrocarbons and materials from $CO_2$ and water.

In contrast to hydrogen, methanol, or other liquid oxygenated hydrocarbon, $CO_2$ may be relatively easy to produce, simple, safe and easy to store and transport and may be easily converted to light chain hydrocarbons. It would therefore be beneficial to provide a system and method to produce light chain hydrocarbons from readily available sources without causing further harm to the environment and which does not require the transportation of gaseous feedstocks which are potentially unsafe and which may be expensive.

SUMMARY OF THE INVENTION

The present invention resolves the problems outlined above by providing a system and process for the synthesis of light chain hydrocarbons from carbon dioxide sources such as calcium carbonate.

The present invention relates to a process for synthesizing light chain hydrocarbons from methanol produced from a calcium carbonate material including the following steps (i) liberation of a carbon dioxide gas from the heated calcium carbonate feedstock;
(ii) filtering impurities from the extracted carbon dioxide of step (i);
(iii) reacting the extracted carbon dioxide obtained in step (i) with a dihydrogen gas to form a methanol feedstock;
(iv) isolating the cooled methanol feedstock formed in step (iii);
(v) catalytically converting at least part of the methanol feedstock obtained in step (iii) at elevated temperature and pressure into aliphatic and aromatic liquid hydrocarbons; and
(vi) isolating the decompressed liquid hydrocarbon product obtained in step (v).

The present invention also relates to a system for synthesizing the light chain hydrocarbon from a calcium carbonate source material including A system for synthesizing a light chain hydrocarbon from a calcium carbonate feedstock, said system including providing a resealable chamber adapted to heat the calcium carbonate feedstock, liberating a carbon dioxide gas which is received by an intermediate holding vessel which is in communication with the resealable chamber, the vessel being generally adapted to receive and cool the liberated carbon dioxide gas and capturing any excess energy from the liberated carbon dioxide gas. The liberated carbon dioxide gas, along with a supply of dihydrogen gas is received by a supply structure into the intermediate holding vessel, the vessel being adapted to release a formed gaseous mixture to a separator adapted to receive and separate the gaseous mixture from the intermediate holding vessel, the separator also separating impurities and excess energy allowing the gaseous mixture to pass through the separator to a compressor having an inlet port separated along a gas feed passageway from an outlet port, the inlet port being in communication with the separator and adapted to receive the gaseous mixture from the separator. The gas is generally compressed along the gas feed passageway through said outlet port. A second stage reactor in communication with a heat exchanger which is adapted to receive the compressed gaseous mixture from the compressor for reaction at the second stage reactor, wherein the second stage reactor is generally adapted to produce methanol as a result of the reaction between the compressed gaseous mixture and a dihydrogen gas supply received within the second stage reactor. A heating supply which is heated at least in part by said captured excess energy, said heating supply adapted to heat said methanol. A third stage reactor receives the heated methanol, the third stage reactor having a catalyst and adapted for synthesizing the light chain hydrocarbon from a reaction between said methanol and a hydrogen supply.

BRIEF DESCRIPTION OF THE DRAWINGS

The drawings constitute a part of this invention and include exemplary embodiments of the present invention and illustrate various objects and features thereof.

DETAILED DESCRIPTION

Introduction

As required, detailed embodiments of the present invention are disclosed herein; however, it is to be understood that the disclosed embodiments are merely exemplary of the invention, which may be embodied in various forms. Therefore, the specific compositions, methods, structural and functional details disclosed herein are not to be interpreted as limiting, but merely as a basis for the claims and as a representative basis for teaching one skilled in the art to variously employ the present invention in virtually any appropriately detailed structure.

System and Process for Hydrocarbon Synthesis.

Figure 5:
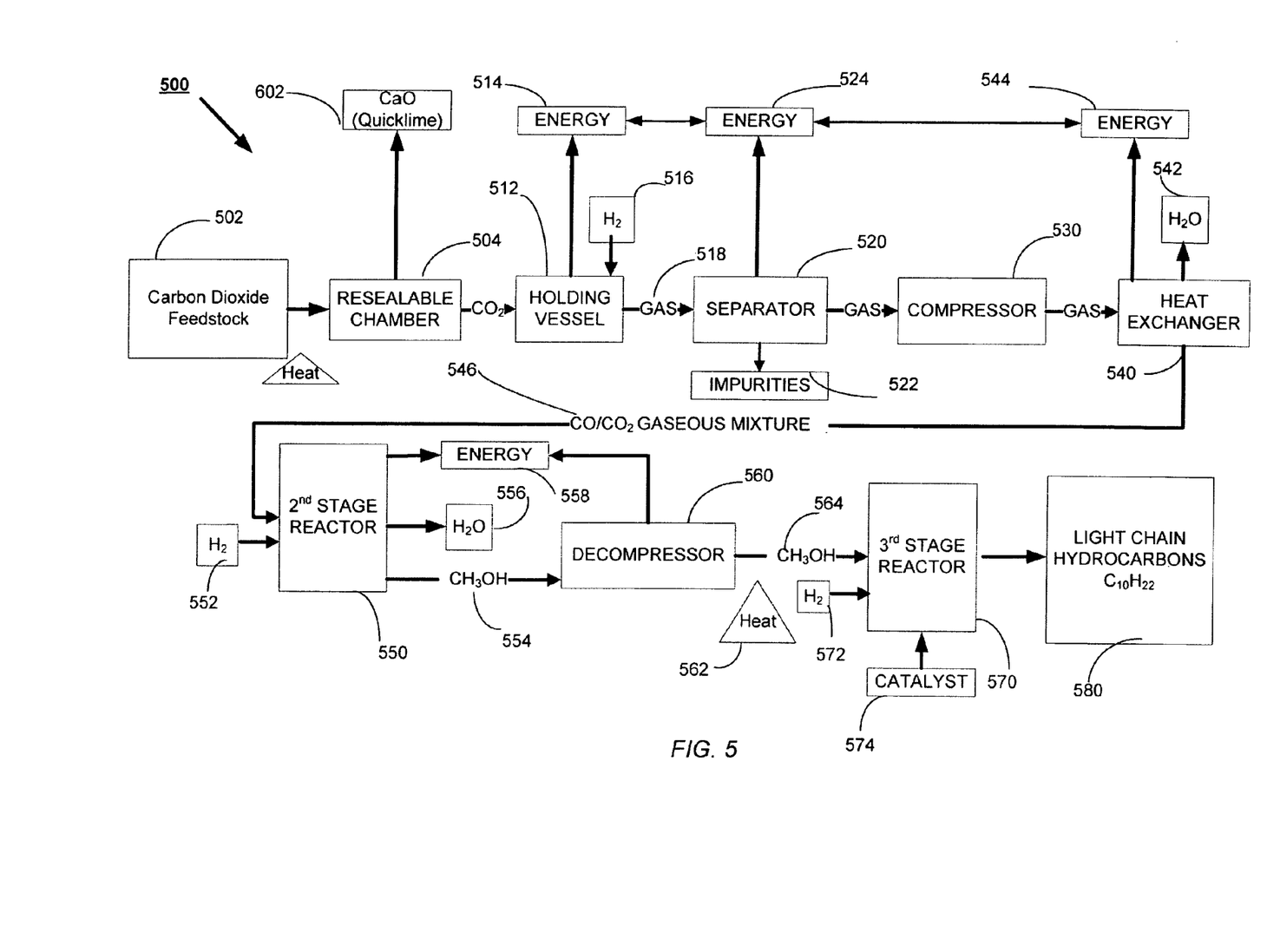
FIG. 5 is a block diagram of the system in accordance with the present invention.

The present invention provides a system 500 and process 60 and method for synthesizing light chain hydrocarbons generally referred to as numeral 60 which uses a readily available feedstock such as but not limited to calcium carbonate to produce hydrocarbons from methanol as illustrated in the following general chemical reaction equation:

$$CO_2 + 3H_2 \rightarrow CH_3OH + H_2O \tag{I}$$

$$nCH_3OH_{with\ catalyst} \rightarrow nH_2O + \text{Light Chain Hydrocarbon} \tag{II}$$

The economy of the process may be characterized by the use of industrial by-products such as $CO_2$, $SO_2$. Various byproducts from various portions or the entire synthesis reaction sequence 60 may be captured during or after the process 60 for utilization within a portion or portions of the process 60 or for commercial uses outside the described process.

In accordance with the scope of the invention each part may be used alone or in combination with other parts or alone or in combination with a thermal, mechanical, chemical or electrical process for synthesizing the light chain hydrocarbon.

Figure 1:
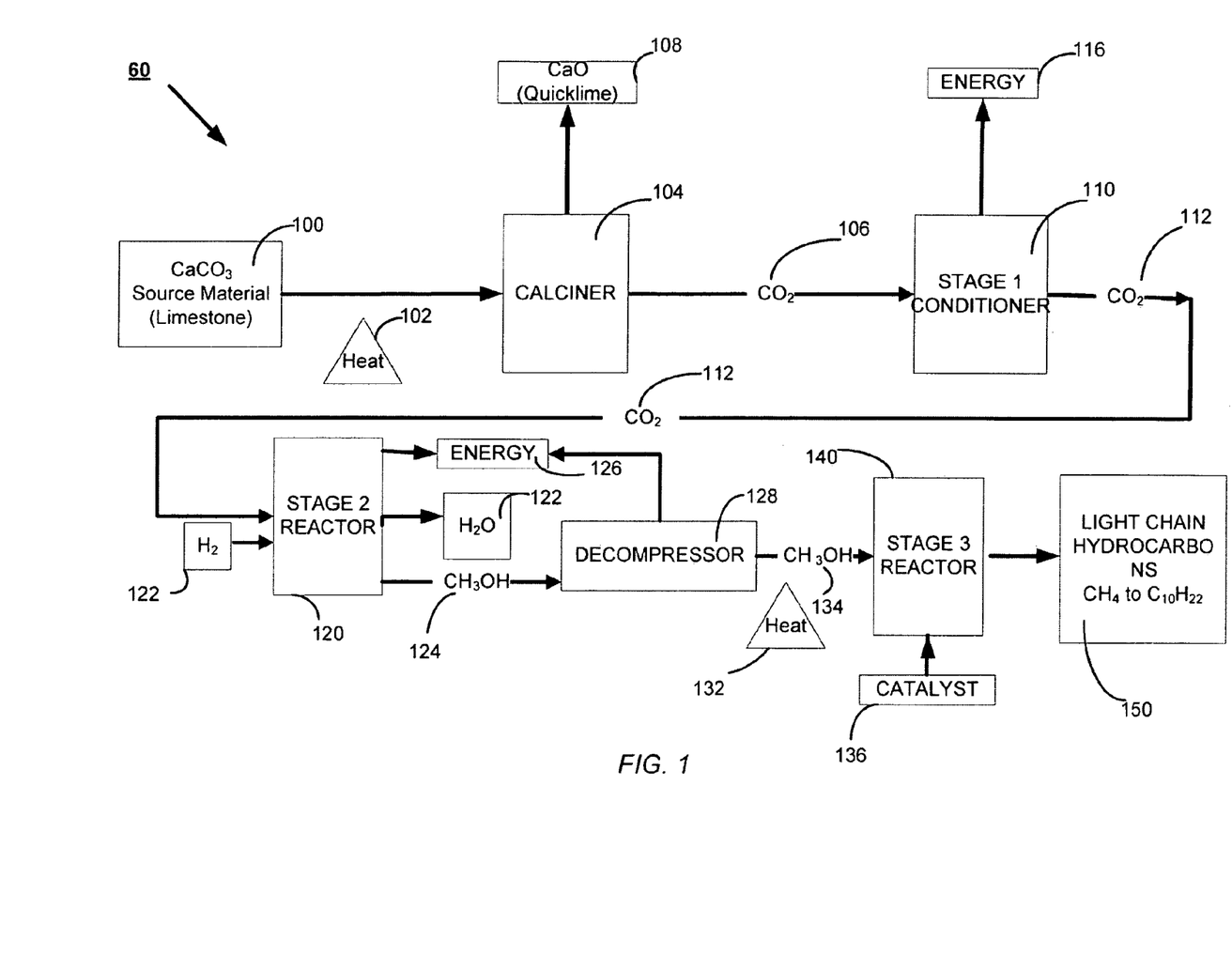
FIG. 1 is a block diagram of the overall process for hydrocarbon synthesis in accordance with one embodiment of the present invention.

Referring now to the drawings in general and FIG. 1 in particular, in one embodiment of the present invention, a hydrocarbon synthesis system 500 and process 60 for creating light chain hydrocarbons from $CO_2$ via methanol. Generally, the reaction sequence 60 begins with carbon dioxide as the feedstock. The source for carbon dioxide may be limestone ($CaCO_3$) because of its common availability. Alternatively, other feedstocks can provide the $CO_2$ such as various exhaust sources such as fossil fuel-burning power plants, various industrial plants, and even processes that derive $CO_2$ from the air or seawater.

Figure 1A:
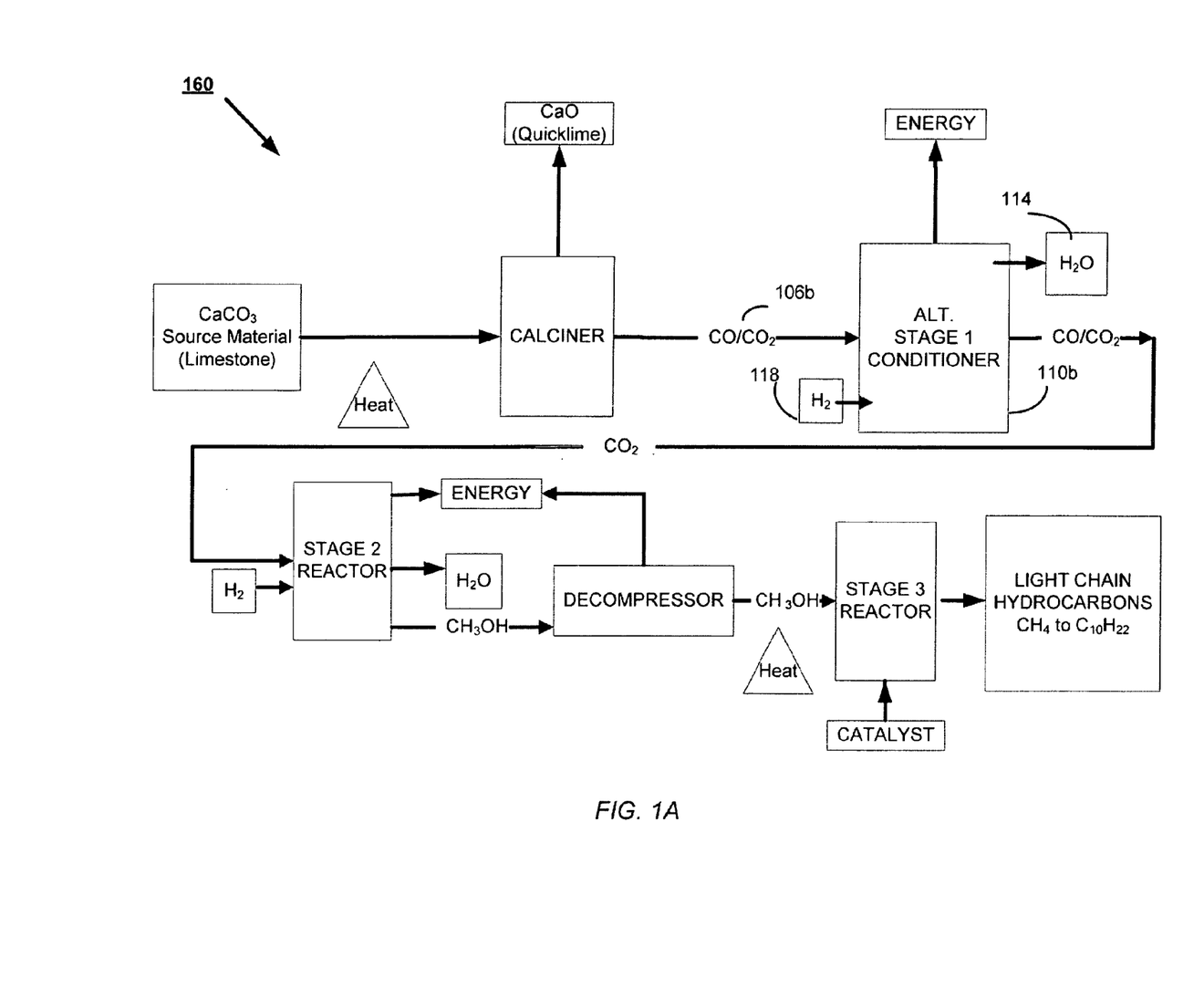
FIG. 1A a block diagram of an alternative aspect in accordance with the present invention.

As illustrated, in FIG. 1, the limestone source material 100 is decomposed at the calciner 104 producing carbon dioxide gas 104 which is separated for further processing. The carbon dioxide gas 104 may then be conditioned within the Stage 1 Conditioner 110, resulting in a carbon dioxide gas 112, or a mixture of carbon monoxide and carbon dioxide gases 112b as illustrated in FIG. 1A. The carbon dioxide 112 or carbon monoxide and carbon dioxide mixture 112b may then be further reacted 120 within the Stage 2 Reactor 120 to produce methanol 124. The methanol 124 may be purified and separated for use in other industrial processes or for use as a reactant in further steps in the synthesis process 60. Finally, the methanol reactant 134 and a catalyst 136 are reacted in a Stage 3 Reactor 140 to produce a mixture of light chain hydrocarbons 150.

The calciner 104 may be a typical horizontal industrial direct-fired rotary kiln constructed of mild steel and fitted with a heat shield covering the first 6 meters of the kiln. The next 18 meters of the kiln comprise a lifting section, and the final three meters of the kiln comprise a discharge section to separate the solid product, CaO from the processed off-gas, $CO_2$. The calciner 104 may be fired with natural gas and forced air, with raw carbonate material entering via a feed chute. For example, reference is made to *Industrial and Engineering Chemistry Research*, Vol. 38, pp. 1001-1023, which describes process flow control in such a calciner.

Alternatively, the calciner 104 may have a "D-D" geometry vertically arranged. Such a calciner 104 may consist of a cylinder and throat having diameters of around 4.18 meters and 2.8 meters, respectively, with a total height of 18.3 meters. Using such an arrangement, the reaction zone may be in communication with the inlet of the calciner 104, through a passageway having a diameter of about 1.54 meters through which passes forced air, pulverized coal and carbonaceous material. Using such a calciner may provide capacity for 2000 tuns per day (1,908,000 liters per day). For example, reference is made to *Industrial and Engineering Chemistry Research*, Vol. 44, pp. 3033-3041, which describes a reaction process occurring in such a calciner.

For the process described herein, the calciner may be fitted with a heat transfer device to recapture excess heat for further use in the process, and a device for the capture of the emitted $CO_2$ gas.

One embodiment of this process for synthesizing light chain hydrocarbons from a limestone or $CaCO_3$ source is generally based upon the following sequence of chemical reaction equations:

$$CaCO_3 \rightarrow CaO + CO_2 \tag{III}$$

$$CO_2 + 3H_2 \rightarrow CH_3\text{—}OH + H_2O \tag{IV}$$

$$CH_3\text{—}OH_{with\ catalyst} \rightarrow \text{Light Chain Hydrocarbons} \\ (CH_4\ \text{to}\ C_{10}H_{22}) + H_2O \tag{V}$$

Referring primarily to FIG. 1, the process starts when the $CaCO_3$ source material 100 is heated 102 in a calciner 104 at a suitable temperature and pressure to maximize the gaseous carbon dioxide 106 yield, preferably from about 500° C. to 900° C. at about one atmosphere. In addition to the produced carbon dioxide gas 106, quicklime (CaO) 108 may be generated by the oxidation reaction within the calciner 104 and captured or recycled for additional use.

If the quicklime is captured or recycled for additional use, it can be combined with additional $CO_2$ within the air, an industrial process, seawater or other sources, yielding additional $CaCO_3$ source material 100, for further oxidation within the calciner 104.

Many suitable types of energy sources may be used to provide heat 102 for the reaction and other reactions in the process, including thermal, mechanical, electrical or nuclear energy. For example, the waste heat from a solar plant producing dihydrogen by thermal decomposition can be used to drive a portion or portions of the process. An additional example of a suitable energy source is a pebbled bed, gas cooled, nuclear reactor. These examples may contribute to the efficiency of this invention.

The reactant $CaCO_3$ source material 100 provides the $CO_2$ for the synthesis reaction process 60. It may be purchased or derived from many suitable sources, including limestone, dolomite, or other carbonate minerals. The carbonate mineral sources are advantageous because they are natural and abundant, decreasing the "footprint" of the overall synthesis process 60. The temperature at which the decomposition step should occur varies depending on the source material. For example, in one step of the process 60, the temperature for the decomposition step within the calciner 104 may be about 890° C. if limestone is used and about 725° C. for dolomite limestone.

Alternatively, the $CO_2$ reactant may be provided as a byproduct of another industrial process or may be extracted from the atmosphere. With respect to collecting $CO_2$ for the synthesis reaction 60 from industrial flue gases 300, it may be preferable to synthesize the $CO_2$ in the location where the $CO_2$ is released from the site of the industrial process. Alternatively, the released $CO_2$ may be transported to the location of the synthesis reaction. Using the $CO_2$ produced as a byproduct from the industrial process has distinct advantages relating to the objects of this invention. For example, by using an industrial byproduct from a separate industry, such as the cement industry, recycling of waste is promoted. Alternatively, the $CO_2$ may be extracted from the atmosphere, contributing to a decrease in net $CO_2$ emissions into the atmosphere.

Capturing $CO_2$ from the atmosphere using basic absorbents such as calcium hydroxide or potassium hydroxide in reaction with $CO_2$ may form calcium carbonate and potassium carbonate respectively. Due to the low concentration of $CO_2$ in the atmosphere, approximately only 0.037%, large volumes of air should be directed towards the sorbent material, this being potentially achieved using convection, for example, mechanically with a hyperbolic tower, vortex or other structural or mechanical means for injecting air towards the sorbent material. After the $CO_2$ is captured by the absorbent, the $CO_2$ may be recovered by desorption, through heating, vacuum, electrochemically or using other means. For example, the sorbent may be introduced into the calciner 104 as calcium carbonate for release of the $CO_2$ in exothermic reaction in which the $CO_2$ is reacted with an adequate base, allowing the heat to be recycled. While the oxidation reaction is exothermic, yielding energy as a result of the calcination, the energy needed for recovery of the $CO_2$ is relatively high when using calcium carbonate or sodium carbonate, in comparison with other known sorbents such as potassium. In addition, when using potassium, the electrolysis of potassium carbonate in water may also produce dihydrogen, which may be captured and used in another step of the process 60.

Because the source material 100 may vary, and various catalysts may be used under varying conditions, the resultant $CO_2$ gas stream 106 may be contaminated. Therefore, it may be beneficial to remove primary contaminants from the resultant gas stream 106 before proceeding with the additional synthesis process 60, which may include one or more of the following: nitrogen, oxygen, nitrogen oxides, calcium oxide, sulfur compounds, halogens, and heavy metals. Approaches to remove these impurities at various steps in the sequence may include but is not limited to separation techniques such as dissolving the contaminated compounds in water, filtration, absorber beds, electrostatic precipitation, wet scrubbing, molecular filtration, or reaction with various catalysts.

By way of example, to remove oxygen contaminates, one may inject dihydrogen or natural gas into the resultant gas stream 106 to convert the oxygen contaminate to $H_2O$ and/or $CO_2$. Additionally, charcoal or carbon may be mixed with the $CaCO_3$ prior to heating in order to convert any excess oxygen contaminates to carbon dioxide or carbon monoxide. Methods for removing nitrogen oxide contaminates may include reacting it with carbon monoxide, ammonia, or platinum/palladium/rhodium catalysts. Methods to remove calcium oxide may include a wet scrubber, electrostatic precipitation, or mixing it with liquid water. Obviously the above described examples are meant as illustrations of some ways to remove contaminates, but is not an exclusive listing as one of ordinary skill may utilize a number of known methods to remove contaminants from the $CO_2$ gaseous stream 106.

The resultant products from the decomposition reaction at the calciner 104 may include quicklime 108 and gaseous carbon dioxide 106 or a mixture of carbon monoxide and carbon dioxide gases 106b as illustrated in FIG. 1A. The $CO_2$ gas stream 106 exiting from the calciner 104 may then be conditioned by the Stage 1 Conditioner 110, illustrated in FIG. 2. Conditioning may include cooling 110a the $CO_2$ gas stream 106, filtering 110b and removing any unwanted impurities 110d. The heat energy 116b from the conditioned $CO_2$ gas stream 112 exiting the calciner 104 may be captured and stored for use by other step or steps within the synthesis reaction sequence 60. Filtration 110b may be accomplished by a variety of suitable means known in the art, including wet or dry filters, scrubbers, or using catalysts to chemically separate out any impurities. Once conditioned, the $CO_2$ gas stream 112 may then be transmitted to the Stage 2 Reactor 120.

Figure 2:
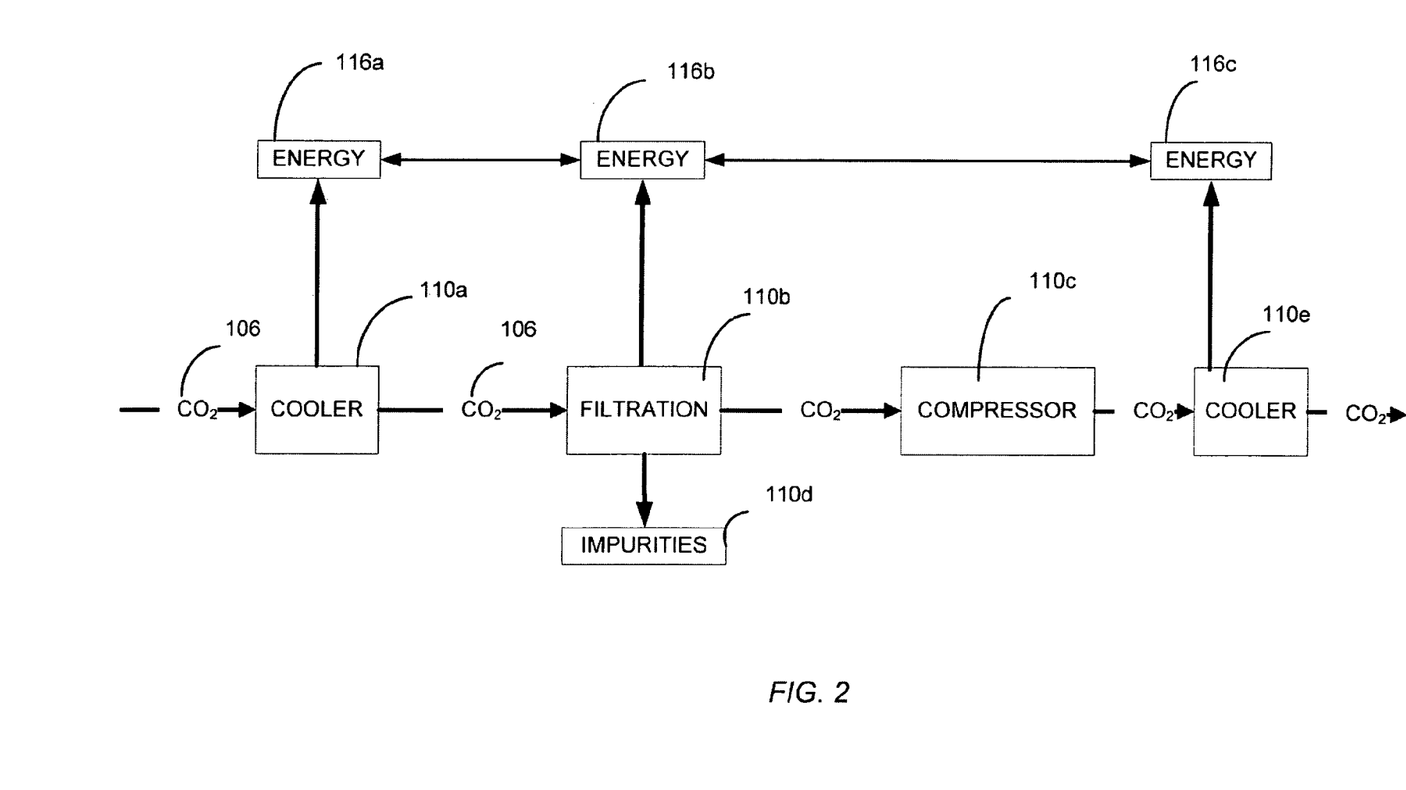
FIG. 2 is a block diagram of the Stage 1 Conditioner in accordance with one aspect of the present invention.
Figure 2A:
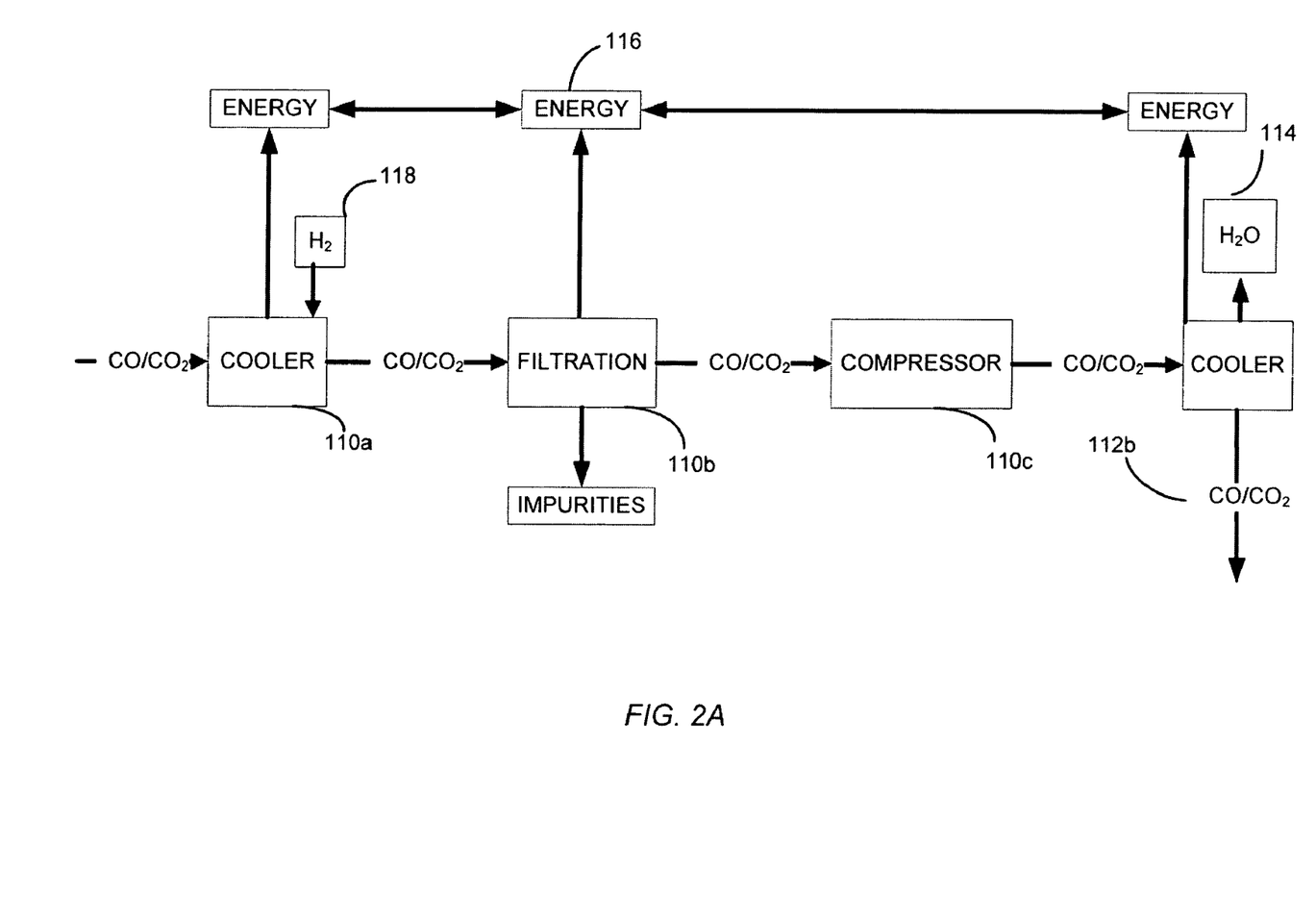
FIG. 2A is a block diagram of the Alternative Stage 1 Conditioner in accordance with an alternative aspect of the present invention.

Alternatively, as illustrated in FIG. 1A, the calciner 104 may produce a mixture of $CO/CO_2$ gases 106b in addition to quicklime 108. The mixture 106b may be conditioned and undergo a reverse-gas water shift reaction at the Alternative Stage 1 Conditioner 110b for use within the synthesis reaction sequence 60. As illustrated in FIG. 2A, within the Alternative Stage 1 Conditioner 110b, the mixture 112b may be cooled 118, filtered 110b removing any unwanted contaminates and compressed 110c. After a second stage cooling 110d, the conditioned mixture 112b exits the Alternative Stage One Conditioner 110b at a suitable temperature and pressure. In one example the conditioned mixture 112b may be about 250° C. at about 50 atmospheres. As a result of passing the mixture 112b through the compressor 110c, some of the $H_2O$ vapor 114 may liquefy for drainage from the Alternative Stage 1 Conditioner 110. This liquid water 114 may be used in additional steps within the synthesis reaction process 60, including in the wet filtration system to remove any undesired contaminants.

In association with the Alternative Stage 1 Conditioner 110b, the reactant CO/CO₂ mixture 106b may undergo an endothermic reverse water gas shift reaction for the conversion to CO in which a dihydrogen gas 118 is reacted with the CO/CO₂ mixture 106b resulting in water and additional carbon monoxide. In advance of the reaction, the mixture 106b may be cooled 110a before being reacted with dihydrogen gas 118. Alternatively, the CO/CO₂ gas stream 106b may be reacted with dihydrogen gas 118 before being cooled 110a. However, because the reverse water, gas-shift reaction is an endothermic process, generally requiring 9.8 kcal per mol, it may be preferable to mix the dihydrogen with the CO₂ prior to cooling. The reverse water gas shift reaction associated with the Stage 1 Conditioner 110, is generally represented by the following chemical equation:

$$CO_2 + H_2 \rightarrow CO + H_2O \quad (VI)$$

The products formed as a result of the Stage 1 Conditioner 110 may include a pressurized CO₂ gas 112, water 114, energy 116 and any impurities. Alternatively, the products formed as a result of the Alternative Stage 1 Conditioner may include pressurized CO/CO₂ gaseous mixture 112b, water 114, energy 116 and any impurities.

The dihydrogen gas reagent 118 should be generally undiluted and may come from many suitable sources, such as but not limited to, electrolysis of water, thermal decomposition of water and the sulfur-dioxide iodine cycle. In electrolysis, electrical current is used to dissociate water into dihydrogen and oxygen. The efficiency of electrolysis in large industrial units may approach 60 percent and is represented by the following reaction:

$$2H_2O \rightarrow 2H_2 + O_2 \quad (VIII)$$

To get dihydrogen 106 via the thermal decomposition of water, the water temperature should be raised to about 1800° C., thermal decomposition beginning at about 1530° C. Excess heat from this process can also be used to drive other reactions in this process 60, such as breaking down the calcium carbonate 100. The efficiency of thermal decomposition may reach 50% or more.

Figure 3:
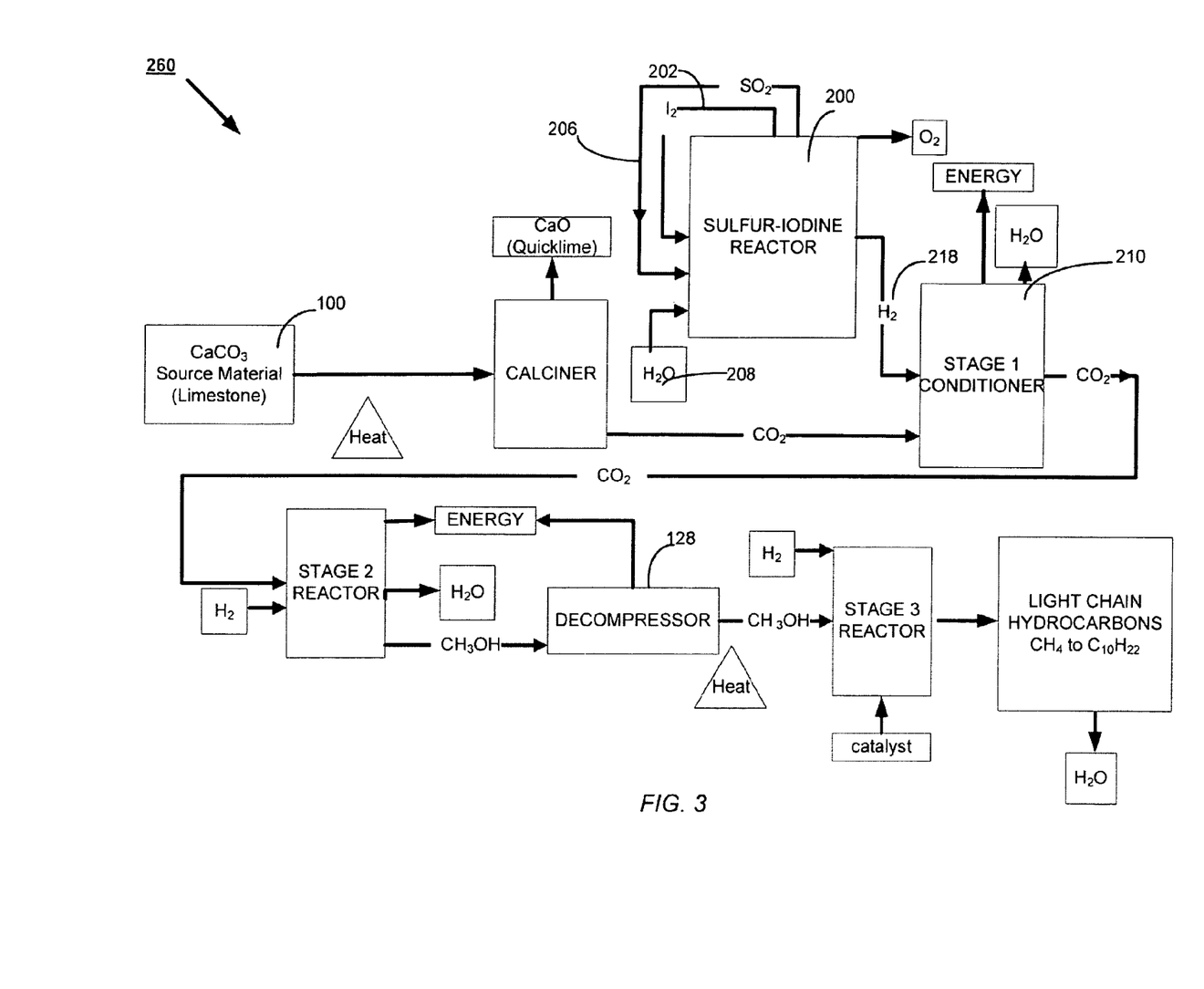
FIG. 3 is a block diagram of the overall process of a second alternative embodiment of the present invention.
Figure 4:
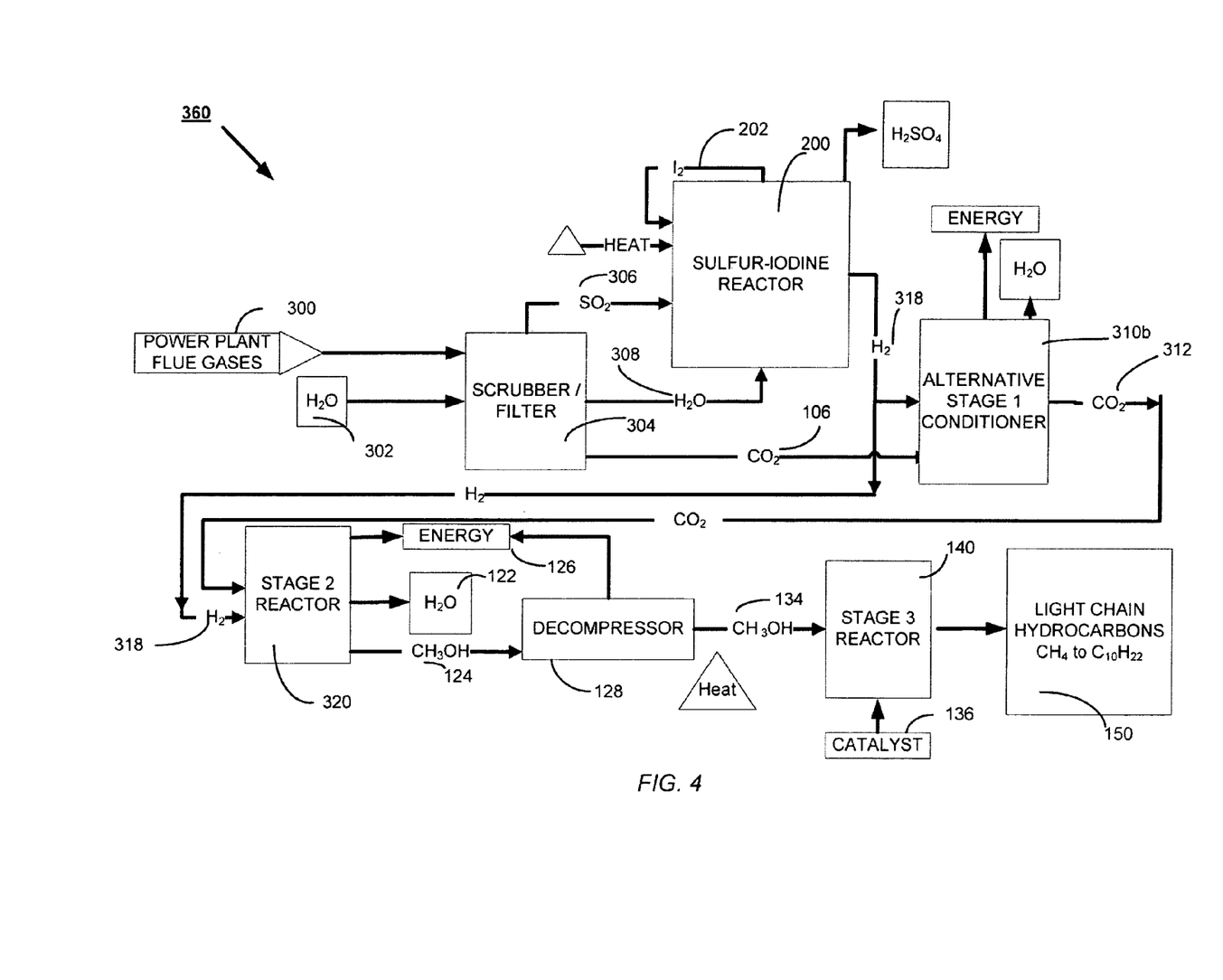
FIG. 4 is a block diagram of the overall process of a third alternative embodiment of the present invention.

In accordance with another alternative aspect of the synthesis reaction sequence 260, a chemical cycle, including a sulfur-dioxide iodine cycle 200 illustrated in FIG. 3 may be utilized apart from and/or in combination with capturing CO₂ from industrial waste illustrated in FIG. 4. As illustrated below, the sulfur-dioxide iodine reaction 200, involves reacting SO₂ 206, iodine 202 and water 208 in an exothermic reaction to form sulfuric acid and hydrogen iodide. At temperatures above 350° C., the HI may decompose to dihydrogen 218 and iodine 202 allowing the iodine to be recycled for later use. Sulfuric acid may then decompose as temperatures increase above 850° C. into SO₂ 206, water and oxygen. Because the SO₂ 206 and iodine 202 are recycled, the overall sulfur-iodine reaction 200 proceeds, as in equation (VIII) generally according to the following chemical equations:

$$I_2 + SO_2 + 2H_2O \rightarrow 2HI + H_2SO_4 \text{ (about 120° C.)} \quad (IX)$$

$$H_2SO_4 \rightarrow SO_2 + H_2O + (\tfrac{1}{2})O_2 \text{ (about 850° C.)} \quad (X)$$

$$2HI \rightarrow I_2 + H_2 \text{ (about 350° C.)} \quad (XI)$$

Some of the energy needed for this reaction 200 may be obtained from other steps in the alternative synthesis reaction sequence 260. Furthermore, because the SO₂ 206 and iodine 202 in this reaction 200 can be recycled, the sulfur-dioxide iodine reaction 200 may continue until the water supply 208 and energy necessary for the reaction 260 are depleted. The dihydrogen may also be separated and conditioned at the Stage 1 Conditioner 210, including removing any impurities from the dihydrogen gas 218 using known filtering methods including via a molecular filter.

Referring to FIG. 4 an alternative embodiment of the synthesis reaction sequence 360 may include utilizing the products or waste products from other industrial processes, such as but not limited to using power plant flue gases 300 to generate a CO₂ gas stream 106 which may be conditioned 310 and reacted within the Stage 2 Reactor 320, producing methanol 124 which may be synthesized into the light chain hydrocarbons 150. Some typical products contained within power plant flue gases 300 may include, but is not limited to, sulfur dioxide, carbon dioxide, water, and other contaminants.

In the illustrated embodiment, the power plant flue gases 300 may be collected with for example, but not limited to, a scrubber/filter 304 to separate the flue gases 300 generally into sulfur dioxide 306, water 308, and carbon dioxide 106. The sulfur-iodine cycle 200 may optionally be added to this alternative reaction process 360 in which the sulfur dioxide 306, water 308, and iodine 202 are reacted in a reactor such as, but not limited to, a thermonuclear reactor 200 yielding dihydrogen 318. The produced dihydrogen 318 is illustrated as a reagent within the Alternative Stage 1 Conditioner 310b associated with a syn gas reaction to produce CO/CO₂ mixed gases and within the Stage 2 Reaction 320.

The stage-2 reactor 120 generally converts a mixture of carbon dioxide 312 and dihydrogen 318 to methanol 124. The production of methanol 124 may be summarized in the following exothermic chemical reaction with heats of reaction equal to −11.9 kcal per mol:

$$3H_2 + CO_2 \rightarrow CH_3\text{—}OH + H_2O \quad (XII)$$

The crude product stream, consisting of methanol 124 and water 122 (at 36 wt. %) may be taken directly into the stage three reactor 140, but the preferred embodiment is the separation of water from the methanol product, which may be done using known separation techniques.

By way of example, the conversion of carbon dioxide is described in a preliminary report by Ipatieff and Monroe, using a copper-alumina (Cu—Al₂O₃) catalyst to affect the transformation. The reaction was performed at pressures from 117 to 410 atmospheres, temperatures ranging from 282-487° C., and with variations in dihydrogen to carbon dioxide ratio and catalyst composition. Specifically, carbon dioxide was converted to 94.3% methanol, 2.5% ethanol, 2.0% methane, and 0.0% carbon monoxide, with 3.3% carbon dioxide recovery using the following conditions: Cu:Al₂O₃ ratio of 8:92 (weight %), a furnace temperature of 300° C., a catalyst temperature of 282° C., at a pressure of 409 atm.; the H₂:CO₂ ratio was 4.3:1. The mechanism of the transformation is proposed to proceed initially via the reduction of carbon dioxide to formaldehyde. The formaldehyde then interacts with the alumina catalyst to provide an intermolecular oxidation and reduction reaction that forms methanol and formic acid via the reaction:

$$2H_2CO + H_2O \rightarrow CH_3OH + HCOOH \quad (XIII)$$

The formic acid formed in this step may decompose via the following reactions to produce carbon dioxide and dihydrogen or carbon monoxide and water which may further react to produce methanol.

$$HCOOH \rightarrow H_2 + CO_2 \quad (XIV)$$

$$HCOOH \rightarrow H_2O + CO \quad (XV)$$

Carbon dioxide thus formed may reenter the reaction scheme as noted in equation (XII) above; carbon monoxide may reenter the reaction to produce methanol via its reduction to formaldehyde, which enters the reaction as follows:

$$CO + H_2 \rightarrow H_2CO \quad (XVI)$$

While carbon monoxide formed in this way may be recycled to produce methanol, the addition of carbon monoxide to the initial stream of carbon dioxide leads to a diminished conversion of carbon dioxide and/or carbon monoxide to methanol. Referring to the *Journal of the American Chemical Society*, Vol. 67, pp. 2168-2171, experimental results indicate that a ratio of gases, $H_2:CO:CO_2$, consisting of 15.3:3.1:1.0 mole ratio resulted in methanol (64.0%), ethanol (0.4%), methane (5.6%) and dimethyl ether (1.8%). In this reaction, 2.1% of the CO and 3.2% of the $CO_2$ was recovered, using a catalyst at 299° C. consisting of 28% copper and 72% alumina at a pressure of 409 atm. with a furnace temperature of 300° C. The reaction, consisting of only carbon monoxide, yielded significantly lower yields of methanol, in the range of 39.1% to 42.9%.

The conversion of carbon dioxide to methanol may be described as a process that uses the reverse-water-gas-shift (RWGS) reaction to convert $CO_2$ to CO, and then reduces CO to methanol. On the other hand, carbon dioxide hydrogenation forming methanol via a reverse-water-gas-shift reaction, may be referred to as a "CAMERE process." Based upon experimental results, the overall reaction sequence of the CAMERE process may be the same as above, with the exception that the transformation may be affected by associating the RWGS reaction with the alternative stage-1 reactor prior to the stage-2 reactor, which converts carbon monoxide to methanol. The chemical transformations may be generally illustrated by the following chemical equations:

$$CO_2 + H_2 \rightarrow CO + H_2O \text{ (the RWGS reaction)} \quad (XVII)$$

$$CO + 2H_2 CH_3OH \quad (XVIII)$$

By way of example, *Industrial & Engineering Chemistry Research*, Vol. 38, pp. 1808-1812, incorporated by reference herein, the RWGS reaction (XVII) was conducted having an initial reaction environment of 773 K and 10 atmospheres pressure and a mole per hour feed ratio of $CO_2$ and $H_2$ of 2.30:7.76. The mole per hour ratio of the resulting synthesis gas from this first step (XVII) was composed of 1.40 CO, 0.89 $CO_2$, 6.35 $H_2$, 0.01 $H_2O$, and 0.00 $CH_3OH$. In the second exothermic step (XVIII), the output stream of methanol consisted of a mole per hour ratio of <0.001 CO, <0.03 $CO_2$, <0.002 $H_2$, <0.001 $H_2O$, 1.22 $CH_3OH$, with a heat of reaction generally about −21.7 kcal per mol. The methanol production step may utilize a catalyst which may be, but is not limited to $CuO:ZnO:ZrO2:Ga_2O_3$ (5:3:1:1), or a commercial methanol catalyst composition; the second reactor is held at 523 K and a pressure of 30 atmospheres. The overall synthesis process 360 may result in an overall carbon conversion to methanol of 89%.

The excess energy 126 from the exothermic reaction illustrated above may be captured and stored or used within the synthesis reaction process 360 or for other uses. In addition, as a result of the reaction, the volume of the methanol may decrease. While generally the synthesis gas used to form methanol can be obtained by reforming or partially oxidizing any carbonaceous material, the synthesis process 360 illustrates the use of synthesis gas associated with the alternative stage-1 condition 310b in connection with carbon dioxide/carbon monoxide mixture 312b.

In the homogeneous gas-phase oxidation reaction of the stage-3 reactor 320, methane may be generally reacted with oxygen at high pressures around 30 to 200 atm and high temperatures 200 to 500° C. As the oxygen concentrations in the system decrease, methanol selectivity increases. Some results indicate that under cold flame conditions (450° C., 65 atm, less than 5% $O_2$ content) 75-80% selectivity in methanol formation is achieved with an 8-10% conversion rate. Based upon further testing data, it appears that factors affecting the reactions such as reactor design, shape or duration of the reaction has limited effect on the selectivity of the methanol formation.

The produced methanol 124 from the Stage 2 Reactor 112 may be heated 132 and decompressed 128, preferably to about 340° C. at about five atmospheres, for receipt by the Stage 3 Reactor 140.

The energy recovered by the decompressor 128 may be used to provide power for compression within Stage 1 110 of the synthesis reaction sequence 60. The low pressure methanol 134 provided by the decompressor 128 may be utilized in the Stage 3 Reactor 140 to produce light chain hydrocarbons 150.

The stage-3 reactor 140 provides for the conversion of methanol to hydrocarbons. The overall reaction to produce light chain hydrocarbons 150 may be denoted as follows:

$$nCH_3OH_{\text{with catalyst(s)}} \rightarrow (CH_2)n + \text{(light chain hydrocarbons)} + nH_2O \quad (XIX)$$

The process may be broken down into steps including 1) the equilibration of methanol with water and dimethyl ether; 2) the interaction of these components with the catalyst(s); 3) the formation of olefins at the catalyst; 4) the conversion of the olefins to aliphatic light chain hydrocarbons. A zeolitic catalyst 136, for example ZSM-5, may be used as the catalyst in the stage-3 reaction 140; the addition of a co-catalyst, for example toluene, xylene or other methyl benzenes also may be included in the stage-3 reaction 140. *Accounts of Chemical Research*, Vol. 36, pp. 317-326, which is incorporated by reference herein, reviews some mechanistic considerations of the methanol to hydrocarbon transformation.

For example, methanol may be quantitatively (100%) converted at 371° C. (1 atmosphere, 1.0 liquid hourly space velocity) to a mixture of hydrocarbons, with the major fractions being Propane (16.2%), iso-butane (18.7%), toluene (10.5%), xylenes (17.2%); the balance being other aliphatic and aromatic hydrocarbons. The use of zeolite catalysts is helpful in the conversion of methanol and other oxygen containing compounds to hydrocarbons as discussed by *Journal of Catalysis*, Vol. 47, pp. 249-259, as incorporated herein.

Methanol may also be converted to gasoline by passing pure methanol at one atmosphere over a zeolite catalyst at an inlet temperature of 700° F. in a fixed-bed recycle reactor. At a 0.5 per hour weight hourly space velocity and a pressure of 205 psig in the second reactor, the typical hydrocarbon distribution (weight %) is as follows:

methane, ethane, and ethylene (1.5); propane (5.6); isobutene (9.0); n-butane (2.9); propylene and butenes (4.7); $C_{5+}$ aliphatic hydrocarbons (49.0); aromatics (27.3). However, temperature and pressure conditions during the synthesis reaction process 60 effect the conversion of methanol to hydrocarbons as discussed in *Industrial Engineering Chemistry: Process Design and Development*, Vol. 17, pp. 255-260, which is incorporated herein by reference.

Alternatively, chromium oxide and/or zinc oxide catalysts can be used where the carbon dioxide 112 is cooled and compressed to a suitable temperature and pressure such as, but not limited to, around 350 atmospheres and 320° C., allowing the liquid condensate to be drained. The pressurized gas may be mixed with dihydrogen in an alternative stage 2 reactor 120b which includes a chromium-zinc oxide catalyst, which is used to produce the methanol 124 for use by the synthesis reaction 60 to produce light chain hydrocarbons.

In accordance with a system 500 for hydrocarbon synthesis a carbon dioxide feedstock 502 such as, but not limited to, limestone is heated within a resealable chamber 504 such as, but not limited to a calciner, resulting in a disassociated carbon dioxide 506 and a first byproduct 602 separated from the feedstock 502. An intermediate holding vessel or cooler 512 may be in communication with the sealed chamber 504 and adapted to receive the dissociated carbon dioxide 506, the cooler resulting in the capture and separation of waste energy 514 from the carbon dioxide 506. The cooler 512 may also provide for the introduction of dihydrogen gas 516 into a chamber contained within the cooler 512 for a reverse water gas shift reaction between the dihydrogen gas 516 and the dissociated carbon dioxide 506. A separator also referred to herein as a filtration device 520 is generally adapted to receive the $CO/CO_2$ mixture 518, the filtration device 520 being generally in communication between the cooler 512 and a compressor 530. The filtration device 520 may utilize known separation techniques to remove an impurity 522 and excess energy 524 from the $CO/CO_2$ gas mixture 518 resulting in a filtered $CO/CO_2$ mixture 526. The compressor 530, having an inlet port separated along a gas feed passageway from an outlet port, may pressurize the filtered gas mixture 526 along the gas feed passageway. The gaseous mixture 526 is received at the inlet port and released at the outlet port near the heat exchanger also referred to herein as a second stage cooler 540. The heat exchanger, 540 may condense any water vapor, draining and formed condensate 542 and excess energy 544 from the received compressed gas mixture 532 for potential use by other steps within the reaction sequence 60.

The heat exchanger 540, in communication with the second stage reactor 550, provides a mixed gas 546 for an exothermic reaction with dihydrogen gas 552 within the second stage reactor 550. Methanol 554, water 556 and excess energy 558 may result from the second stage reactor 550, the methanol being received within a decompressor 560. A heating supply or heater 562 in association with the output of the decompressor 560 excites a decompressed methanol 564 exiting the decompressor 560. The heater may utilize at least some of the captured excess energy from various steps within the synthesis reaction process 60. The excited methanol 564 is received by a third stage reactor 570 along with dihydrogen gas 572 in which a catalyst 574, such as but not limited to zeolite, assists in producing a light chain hydrocarbon 580. After formation, the light chain hydrocarbon 580 may be cooled and condensed.

While the invention has been described in connection with specific embodiments thereof, it will be understood that it is capable of further modifications and this application is intended to cover any variations, uses, or adaptations of the invention following, in general, the principles of the invention and including such departures from the present application as come within known or customary practice within the art to which the invention pertains and as may be applied to the essential features herein before set forth.

Having thus described the invention, what is claimed as new and desired to be secured by Letters Patent is as follows:

1. A system for synthesizing light chain hydrocarbons from a calcium carbonate feedstock, said system including:
   (i) a supply of calcium carbonate feedstock;
   (ii) a resealable chamber having a throat, cylinder, and a feed chute said throat transmitting said supply of calcium carbonate feedstock between said feed chute and said cylinder; said cylinder being adapted to heat the supply of calcium carbonate feedstock liberating a carbon dioxide gas;
   (iii) an intermediate holding vessel connected to said resealable chamber, said holding vessel adapted to receive and cool the liberated carbon dioxide gas, capturing any excess energy from the liberated carbon dioxide gas;
   (iv) a hydrogen gas supply structure for introducing a supply of hydrogen gas into the intermediate holding vessel, the vessel adapted to release an uncompressed gaseous mixture;
   (v) a separator connected to said intermediate holding vessel, and spaced opposite said resealable chamber, said separator receiving said uncompressed gaseous mixture separating impurities and excess energy from said uncompressed gaseous mixture as said uncompressed gaseous mixture passes from said intermediate holding vessel to a compressor;
   (vi) a gas feed passageway transmitting a gaseous mixture from said separator to a heat exchanger;
   (vii) said compressor having an inlet port and an outlet port, said inlet port connected to said separator and spaced opposite said heat exchanger, said outlet port connected to said heat exchanger and spaced opposite said separator, said uncompressed gaseous mixture being compressed yielding compressed carbon monoxide/carbon dioxide gaseous mixture and water vapor, said water vapor being separated from the compressed carbon monoxide/carbon dioxide gaseous mixture by said heat exchanger while traveling along said gas feed passageway through said outlet port;
   (viii) the carbon monoxide/carbon dioxide compressed gaseous mixture being transmitted to a second stage reactor from the heat exchanger for reaction at said second stage reactor, to produce methanol as a result of the reaction between the compressed carbon monoxide/carbon dioxide gaseous mixture and a second hydrogen gas supply received within the second stage reactor;
   (ix) a heating supply heated at least in part by said captured excess energy, said heating supply adapted to heat said methanol; and
   (x) a third stage reactor receiving said heated methanol and having a catalyst, said third stage reactor adapted for synthesizing light chain hydrocarbons from a reaction between said methanol and a third hydrogen gas supply.

* * * * *